United States Patent [19]

Miyano et al.

[11] Patent Number: 5,116,950
[45] Date of Patent: May 26, 1992

[54] PROCESS FOR HEAT TREATING FIBRINOGEN

[75] Inventors: Kenmi Miyano, Osaka; Kenji Tanaka; Hideo Nishimaki, both of Nara; Yoshiro Iga, Osaka, all of Japan

[73] Assignee: Green Cross Corporation, Osaka, Japan

[21] Appl. No.: 184,303

[22] Filed: Apr. 21, 1988

[30] Foreign Application Priority Data

Apr. 21, 1987 [JP] Japan .................. 62-98314

[51] Int. Cl.⁵ ................................. C07K 3/00
[52] U.S. Cl. .................... 530/382; 530/380; 435/236
[58] Field of Search ............. 530/382, 380; 435/236

[56] References Cited

U.S. PATENT DOCUMENTS 4,623,717 11/1986 Fernandes et al. .............. 530/380

OTHER PUBLICATIONS (Abstract, Dialog File 225, accession No. 8925134) Chandra et al., U.S. Pat. No. 4,876,241.
(Abstract, Dialog File 351, Accession No. 86-267871/41) Green Cross Corp., JP 61194035.
Murray, Bulletia of the New York Academy of Medicine, vol. 31, No. 5, pp. 341-358 (1955).

*Primary Examiner*—Robert A. Wax
*Assistant Examiner*—Keith C. Furman
*Attorney, Agent, or Firm*—Sughrue, Mion, Zinn, Macpeak & Seas

[57] ABSTRACT

An aqueous solution containing fibrinogen is heated in the presence of at least a sugar, an amino acid and a magnesium salt to thereby inactivate virus(es) possibly contaminating said fibrinogen. According to this process, the inactivation of the contaminating viruses can be achieved while maintaining the activity of the fibrinogen. Thus a highly safe fibrinogen preparation of excellent qualities can be prepared on an industrial scale.

18 Claims, No Drawings

PROCESS FOR HEAT TREATING FIBRINOGEN

FIELD OF THE INVENTION

This invention relates to a process for heat treating an aqueous solution containing fibrinogen to thereby inactivate virus(es) therein.

BACKGROUND OF THE INVENTION

In order to inactivate viruses possibly contaminating a plasma protein such as albumin, Murray et al. proposed a process which comprises heating an aqueous solution of said protein (hereinafter referred to as liquid heating) (cf. The New York Academy of Medicine, 31 (5), 341-358 (1955)). This liquid heating process has been believed to be a very effective virus inactivation method and the effect of the same in the inactivation of a virus has been epidemiologically proved. Thus, liquid heating has been routinely employed up to the present time.

Among plasma proteins, however, only a few including albumin can withstand the above-mentioned liquid heating process and many of those showing high physiological or biological activities are highly sensitive to heat and liable to be thermally denatured, which frequently causes a decrease or loss in activity.

Fibrinogen, which is a plasma protein, is frequently accompanied by a risk of contamination with virus(es), in particular, hepatitis or AIDS virus. Therefore, it should be heated to inactivate these viruses. However, fibrinogen is unstable to heat and thus inactivated during the conventional liquid heating process. Therefore, it has been desired to provide a process for heating fibrinogen to thereby inactivate viruses contaminating the same without inactivating the fibrinogen per se.

SUMMARY OF THE INVENTION

The present invention aims at providing a process for heat treating an aqueous solution containing fibrinogen in which fibrinogen per se is not significantly inactivated, but contaminating viruses therein are completely or at least substantially completely inactivated.

Under these circumstances, the present inventors have examined various processes and consequently found that when an aqueous solution containing fibrinogen is heated in order to inactivate contaminating virus(es) therein such as hepatitis or AIDS virus, the heat stability of the fibrinogen can be extremely elevated by adding at least a sugar, an amino acid and a magnesium salt thereto.

Accordingly the present invention relates to a process for heating fibrinogen which comprises heating an aqueous solution containing fibrinogen in the presence of at least a sugar, an amino acid and a magnesium salt until the virus(es) possibly contaminating said fibrinogen are inactivated.

DETAILED DESCRIPTION OF THE INVENTION

The fibrinogen to be heated in the process of the present invention is or contains a substance exhibiting a biological or physiological activity as fibrinogen, such as those obtained by fractionating plasma proteins.

Examples of these fibrinogen-containing fractions include plasma, the first fraction obtained by Cohn's fractionation with ethanol, cryopaste, a waste fraction remaining after extracting antihemophilic factor from cryopaste and fibrinogen preparations including those preparations satisfying biological products standards.

The concentration of fibrinogen or fibrinogen-containing protein in the aqueous solution thereof to be heated in the process of the present invention may generally range from 0.2 to 6 w/v %, preferably from 1 to 4 w/v %. The concentration of fibrinogen is determined by using fibrinogen determination set manufactured by American Dade Inc.

In the process of the present invention, at least a sugar, an amino acid and a magnesium salt are employed as stabilizers.

As the sugar to be used in the process of the present invention as a stabilizer, monosaccharides, disaccharides and sugar alcohols are available.

Examples of the monosaccharides include glucose, galactose and mannose.

Examples of the disaccharides include sucrose, lactose and maltose.

Examples of the sugar alcohols include xylitol, sorbitol and mannitol

Among these sugars, xylitol is most preferred.

As the amino acid to be used in the process of the present invention, either neutral, acidic or basic ones are available.

Examples of the neutral amino acids include glycine, alanine, proline, tryptophan and serine.

Examples of the acidic amino acids include aspartic acid and glutamic acid.

Examples of the basic amino acids include arginine, lysine and histidine.

Among these amino acids, alanine is most preferred.

The magnesium salt to be used in the process of the present invention is not particularly restricted so long as it is an inorganic salt and soluble in water at a concentration sufficient for achieving the aimed stabilizing effect. Examples thereof include magnesium chloride, magnesium hydroxide, magnesium sulfate, magnesium nitrate and magnesium phosphate.

Among these magnesium salts, magnesium chloride is particularly preferred.

These stabilizers may be added, for example, in the following amounts: 20 to 100 w/v %, preferably 60 to 100 w/v %, of a sugar; 0.1 to 15 w/v %, preferably 5 to 10 w/v %, of an amino acid; and 0.01 mM to 3M, preferably 1 to 100 mM, of a magnesium salt; based on 0.2 to 6 w/v % of fibrinogen solution.

Other stabilizing additives selected from among, for example, neutral salts such as calcium chloride and sodium chloride and organic acid salts such as sodium caproate and sodium citrate may be further added as auxiliary stabilizers to the aqueous solution of fibrinogen. These additives are generally used in a concentration of 0.001 to 1M in the fibrinogen solution.

The pH value of the solution is preferably adjusted to approximately 5 to 8, more preferably 6 to 7.

Since the purity of fibrinogen hardly affects the heat resistance thereof, the stabilizing effect of the process of the present invention substantially remains constant regardless of the purity of fibrinogen. Therefore, the process of the present invention may be applied either to a crude fibrinogen product in the course of preparation or to a final fibrinogen preparation.

The heating conditions are not particularly restricted so long as the fibrinogen per se is not inactivated, but virus(es) contaminating the same are inactivated thereby.

The heating may be usually effected at a temperature of approximately 50° to 80° C. for approximately 10 minutes to 40 hours.

It is preferable to heat the fibrinogen solution to approximately 50° C. for approximately 10 to 40 hours; to approximately 60° C. for approximately 5 to 30 hours; or to approximately 70° to 80° C. for approximately 1 to 15 hours. It is particularly preferable to heat the same to approximately 60° C. for approximately 5 to 30 hours. Routine experimentation can be employed to determine suitable time-temperature combination for use with a specific fibrinogen substance.

Examples of the viruses to be inactivated according to the process of the present invention include those possibly contaminating human plasma proteins, in particular, hepatitis virus and AIDS virus.

The aqueous solution of fibrinogen thus heated may be further purified, if desired, and processed in a conventional manner such as by dialysis, sterilizing filtration, pipetting or lyophilization. Also, various washing steps can be employed to remove stabilizing additives.

The stabilizers used in the process of the present invention exert an effect of highly stabilizing fibrinogen upon liquid heating.

As described above, the heating process according to the present invention makes it possible to inactivate viruses possibly contaminating fibrinogen while almost completely maintaining the activity of fibrinogen per se, thus providing highly safe fibrinogen of excellent qualities.

Accordingly, the process of the present invention is extremely useful in producing a fibrinogen preparation on an industrial scale.

To further illustrate the present invention, and not by way of limitation, the following Examples and Test Example will be given.

EXAMPLE 1

A fibrinogen paste was prepared from the first fraction obtained by fractionating normal human plasma with ethanol according to Cohn's method. The obtained paste was dissolved in a 65 mM citrate buffer solution (pH 6.8) containing 80 w/v % of xylitol, 7 w/v % of alanine and 55 mM of magnesium chloride in such a manner as to give a fibrinogen concentration of 1 w/v %. Then, the resulting solution was heated to 60° C. for 10 hours.

After the completion of the heating, the amount of fibrinogen and the solubility thereof, i.e., the condition of the solution were examined. Further the heated solution was subjected to cellulose acetate electrophoresis and gel filtration. When these data were compared with those of unheated one (having the same composition as described above), no significant difference was observed. This fact suggests that the fibrinogen remained stable under the above heating conditions.

EXAMPLE 2

The procedure of Example 1 was followed except that 90 mM of calcium chloride was further added to the solution as a stabilizer. As a result, it was found that the fibrinogen remained stable upon heating to 60° C. for 10 hours, similar to the case of Example 1.

EXAMPLE 3

A fibrinogen solution was prepared in the same manner as in Example 1 and heat treated to 60° C. for 20 hours. As a result, it was found that the fibrinogen remained stable similar to the case of Example 1.

TEST EXAMPLE 1

A fibrinogen paste was prepared in the same manner as the one described in Example 1. Then various stabilizers shown in Tables 1 to 5 were added thereto and 1 w/v % solutions of fibrinogen in distilled water (pH 5.0 to 7.4) were prepared. Each solution was heated to 60° C. for 20 hours. Then the fibrinogen remaining therein was determined and the residual ratio (%) was calculated based on the fibrinogen content prior to the heating. The determination was carried out by using fibrinogen determination set (manufactured by American Dade inc.) according to the manufacturer's instruction. The appearance of the sample was also evaluated. The results are shown in Tables 1 to 5.

(1) Type of Sugar

TABLE 1

Stabilizing effects of various sugars

| Stabilizer | | | | | |
|---|---|---|---|---|---|
| Amino acid (4 w/v %) | Mg salt (2.93 mM) | Sugar (60 w/v %) | Appearance of solution | Clot | Yield (%) |
| glycine | MgCl₂ | xylitol | white | no | 59 |
| glycine | MgCl₂ | sorbitol | white | a little | 52 |
| glycine | MgCl₂ | mannitol | white | no | 45 |
| glycine | MgCl₂ | sucrose | white | no | 40 |
| glycine | MgCl₂ | glucose | brown | no | 39 |
| glycine | MgCl₂ | galactose | brown | a little | 32 |
| glycine | MgCl₂ | mannose | brown | no | 32 |
| glycine | MgCl₂ | no | white | yes | 0 |
| before heating | | | transparent | no | 100 |

As shown in Table 1, it is clear that the addition of sugar is effective for heat stability of fibrinogen and xylitol, mannitol and sucrose provide particularly excellent stabilizing effect.

(2) Concentration of Sugar

TABLE 2

Stabilizing effects at various sugar concentrations

| Stabilizer | | | Appearance of solution | Clot | Yield (%) |
|---|---|---|---|---|---|
| Amino acid (1.5 w/v %) | Mg salt (3 mM) | Sugar (w/v %) | | | |
| alanine | MgCl₂ | no | white | yes | 0 |
| alanine | MgCl₂ | xylitol 40 | white | yes | 15 |
| alanine | MgCl₂ | xylitol 60 | white | yes | 42 |
| alanine | MgCl₂ | xylitol 80 | white | no | 68 |
| alanine | MgCl₂ | xylitol 100 | transparent | no | 50 |
| before heating | | | transparent | no | 100 |

As shown in Table 2, the sugar concentration effective for stabilizing fibrinogen upon heating is not less than 40 w/v %, particularly about 80 to 100 w/v %.

(3) Type of Amino Acid

TABLE 3

Stabilizing effects of various amino acids

| Stabilizer | | | Appearance of solution | Clot | Yield (%) |
|---|---|---|---|---|---|
| Sugar (60 w/v %) | Mg salt (2.93 mM) | Amino acid (1.5 w/v %) | | | |
| xylitol | MgCl₂ | alanine | white | no | 70 |
| xylitol | MgCl₂ | arginine | white | no | 65 |
| xylitol | MgCl₂ | proline | white | a little | 52 |
| xylitol | MgCl₂ | threonine | white | a little | 61 |

TABLE 3-continued

Stabilizing effects of various amino acids

| Stabilizer | | | Appear- | | |
|---|---|---|---|---|---|
| Sugar (60 w/v %) | Mg salt (2.93 mM) | Amino acid (1.5 w/v %) | ance of solution | Clot | Yield (%) |
| xylitol | MgCl$_2$ | histidine | white | a little little | 59 |
| xylitol | MgCl$_2$ | no | white | yes | 0 |
| before heating | | | white trans-parent | no | 100 |

From the results shown in Table 3, it is clear that the addition of amino acid is effective for heat stability of fibrinogen and alanine and arginine can be preferably used as a stabilizer.

(4) Concentration of Amino Acid

TABLE 4

Stabilizing effects at various concentrations of amino acid

| Stabilizer | | | | | |
|---|---|---|---|---|---|
| Sugar (80 w/v %) | Mg salt (55 mM) | Amino acid (w/v %) | Appearance of solution | Clot | Yield (%) |
| xylitol | MgCl$_2$ | no | white | yes | 0 |
| xylitol | MgCl$_2$ | alanine 1 | white | no | 24 |
| xylitol | MgCl$_2$ | alanine 2 | white | no | 29 |
| xylitol | MgCl$_2$ | alanine 3 | white | no | 34 |
| xylitol | MgCl$_2$ | alanine 4 | white | no | 55 |
| xylitol | MgCl$_2$ | alanine 5 | white | no | 65 |
| xylitol | MgCl$_2$ | alanine 6 | white | no | 70 |
| xylitol | MgCl$_2$ | alanine 7 | white | no | 95 |
| xylitol | MgCl$_2$ | alanine 8 | white | no | 75 |
| xylitol | MgCl$_2$ | alanine 9 | white | no | 70 |
| xylitol | MgCl$_2$ | alanine 10 | white | no | 70 |
| before heating | | | transparent | no | 100 |

As shown in Table 4, it is found that amino acid concentration effective for heat stability of fibrinogen is not less than 1 w/v %, particularly about 4 to 10 w/v %.

(5) Concentration of Magnesium Salt

TABLE 5

Stabilizing effects at various concentrations of magnesium salt

| Stabilizer | | | Appear- | | |
|---|---|---|---|---|---|
| Sugar (80 w/v %) | Amino acid (7 w/v %) | Mg salt (mM) | ance of solution | Clot | Yield (%) |
| xylitol | alanine | no | white | yes | 0 |
| xylitol | alanine | MgCl$_2$ 3 | white | no | 6 |
| xylitol | alanine | MgCl$_2$ 6 | white | no | 11 |
| xylitol | alanine | MgCl$_2$ 11 | white | no | 15 |
| xylitol | alanine | MgCl$_2$ 27 | white | no | 45 |
| xylitol | alanine | MgCl$_2$ 55 | white | no | 95 |
| xylitol | alanine | MgCl$_2$ 110 | white | no | 65 |
| before heating | | | trans-parent | no | 100 |

From the results shown in Table 5, it is found that the magnesium salt concentration effective for heat stability of fibrinogen is not less than 3 mM, particularly about 27 to 110 mM.

TEST EXAMPLE 2

Fibrinogen solutions were prepared in the same manner as in Example 1.

To the resulting solution, each virus shown in Table 6 suspended in a 10 mM isotonic phosphate buffer solution containing sodium chloride (pH 7.0) was added.

After heat treating the mixture at 60° C. for each period shown in Table 6, the infectivity of the virus was determined with plaque technique (as described in Proc. Natl. Acad. Sci. USA, 38, 747-752 (1952)).

The results are shown in Table 6.

TABLE 6

| Virus | Viral Infectivity* | | | | | |
|---|---|---|---|---|---|---|
| | before heating | 60° C. 1 hr. | 60° C. 3 hrs. | 60° C. 5 hrs. | 60° C. 10 hrs. | 60° C. 20 hrs. |
| Vaccinia v. | $1.5 \times 10^5$ | $3.5 \times 10$ | $1.4 \times 10$ | <500 | <500 | <500 |
| Mumps v. | $1.3 \times 10^5$ | $5.2 \times 10^4$ | $3.3 \times 10^4$ | $1.4 \times 10^4$ | $1.9 \times 10^3$ | <50 |
| Herpes simplex v. | $6.1 \times 10^5$ | $8.4 \times 10$ | <50 | <50 | <50 | <50 |
| Chikungunya v. | $2.2 \times 10^6$ | $3.4 \times 10^3$ | <50 | <50 | <50 | <50 |
| Vesicular stomatitis v. | $1.2 \times 10^6$ | $1.3 \times 10^4$ | $1.5 \times 10^2$ | <500 | <500 | <500 |
| Echo v. | $10^{5.4}$ | $10^{3.4}$ | $10^{3.1}$ | $10^{1.7}$ | $<10^{1.5}$ | $<10^{1.5}$ |

Note:
*Infectivities of viruses other than echovirus are expressed in pfu/ml.
Infectivity of echovirus is expressed in TCID$_{50}$/ml.

From the results shown in Table 6, it is apparent that various viruses are inactivated upon the heat treatment of the present invention. Therefore, it is considered that hepatitis or AIDS virus possibly contaminating plasma protein can be inactivated upon the heat treatment according to the present invention.

TEST EXAMPLE 3

A fibrinogen solution was prepared in the same manner as in Example 1.

The resulting solution was heated to 60° C. for 24 hours. Then, the fibrinogen remaining therein was determined and the residual ratio (%) was calculated based on the fibrinogen content prior to the heating.

The results are shown in Table 7.

TABLE 7

| Heating Time (hr) | Residual Fibrinogen (%) |
|---|---|
| 0 | 100 |
| 5 | 98 |
| 14 | 88 |
| 24 | 85 |

As is apparent from the results shown in Table 7, it is found that the fibrinogen is stable upon heating at 60° C. for 24 hours according to the present invention.

While the invention has been described in detail and with reference to specific embodiments thereof, it will be apparent to one skilled in the art that various changes and modifications can be made therein without departing from the spirit and scope thereof.

What is claimed is:

1. In the process for heat treating an aqueous solution of fibrinogen to inactivate virus(es) therein, the improvement which comprises heating an aqueous solution containing fibrinogen in the presence of a stabilizer combination of at least a sugar, an amino acid and a magnesium salt until virus(es) contaminating said fibrinogen are inactivated, wherein said heating is carried out at a temperature of approximately 50° to 80° C. for approximately 10 minutes to 40 hours, and wherein the aqueous solution of fibrinogen comprises 20 to 100 w/v % of the sugar, 0.1 to 15 w/v % of the amino acid and 0.01 mM to 3M of the magnesium salt, each based on 0.2 to 6 w/v % of fibrinogen solution.

2. The process of claim 1, in which the sugar is a monosaccharide, disaccharide or sugar alcohol.

3. The process of claim 1, in which the sugar is a monosaccharide selected from the group consisting of glucose, galactose and mannose.

4. The process of claim 1, in which the sugar is a disaccharide selected from the group consisting of sucrose, lactose and maltose.

5. The process of claim 1, in which the sugar is a sugar alcohol selected from the group consisting of xylitol, sorbitol and mannitol.

6. The process of claim 1, in which the amino acid is a neutral amino acid, an acidic amino acid or a basic amino acid.

7. The process of claim 6, in which the amino acid is a neutral amino acid selected from the group consisting of glycine, alanine, proline, tryptophan and serine.

8. The process of claim 6, in which the amino acid is an acidic amino acid selected from the group consisting of aspartic acid and glutamic acid.

9. The process of claim 6, in which the amino acid is a basic amino acid selected from the group consisting of arginine, lysine and histidine.

10. The process of claim 1, in which the magnesium salt is an inorganic magnesium salt.

11. The process of claim 10, in which the magnesium salt is selected from the group consisting of magnesium chloride, magnesium hydroxide, magnesium sulfate, magnesium nitrate and magnesium phosphate.

12. The process of claim 1, in which the aqueous solution of fibrinogen comprises 60 to 100 w/v % of the sugar, 5 to 10 w/v % of the amino acid and 1 to 100 mM of the magnesium salt, each based on 0.2 to 6 w/v % of fibrinogen solution.

13. The process of claim 1, wherein the pH of the solution is approximately pH 5 to 8.

14. The process of claim 1, wherein the heating is carried out at approximately 60° C. for approximately 5 to 30 hours.

15. The process of claim 1, wherein the virus to be inactivated comprises hepatitis virus or AIDS virus.

16. The process of claim 1, wherein an auxiliary stabilizer is also present.

17. The process of claim 16, wherein the auxiliary stabilizer is selected from the group consisting of calcium chloride, sodium chloride, sodium caproate and sodium citrate.

18. In the process for heat treating an aqueous solution of fibrinogen to inactivate virus(es) therein, the improvement which comprises heating an aqueous solution containing fibrinogen in the presence of a stabilizer combination of at least a sugar, an amino acid and a magnesium salt until virus(es) contaminating said fibrinogen are inactivated, wherein the heating is carried out at approximately 70° to 80° C. for approximately 1 to 15 hours.

* * * * *